(12) United States Patent
Chapuis et al.

(10) Patent No.: US 8,183,194 B2
(45) Date of Patent: May 22, 2012

(54) CARBOXYLIC DERIVATIVES AS VIOLET AND/OR WOODY ODORANT

(75) Inventors: Christian Chapuis, Mies (CH); Hervé Pamingle, Versoix (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/255,298

(22) PCT Filed: Mar. 30, 2010

(86) PCT No.: PCT/IB2010/051367
§ 371 (c)(1),
(2), (4) Date: Sep. 8, 2011

(87) PCT Pub. No.: WO2010/116286
PCT Pub. Date: Oct. 14, 2010

(65) Prior Publication Data
US 2012/0004154 A1 Jan. 5, 2012

(30) Foreign Application Priority Data
Apr. 6, 2009 (WO) .................. PCT/IB2009/051432

(51) Int. Cl.
*C11D 3/50* (2006.01)

(52) U.S. Cl. .............. 510/106; 512/22; 558/430; 560/1; 560/24

(58) Field of Classification Search .............. 510/106, 510/107; 512/22; 558/430; 560/1, 124
See application file for complete search history.

(56) References Cited

U.S. PATENT DOCUMENTS

| | | | |
|---|---|---|---|
| 5,288,702 A | 2/1994 | Ogura et al. | 512/24 |
| 7,384,897 B1 | 6/2008 | Narula et al. | 510/106 |

FOREIGN PATENT DOCUMENTS
EP   0 456 932 B1   11/1991

OTHER PUBLICATIONS

International Search Report and Written Opinion of the International Searching Authority for application No. PCTAB2010/051367, Jun. 30, 2010.
Barakat et al., "Synthesis, olfactory evaluation and determination of the absolute configuration of the β- and γ-Iralia isomers," Tetrahedron: Asymmetry, 19:2316-2322 (2008).
Chapuis et al., "Preparation of Optically Active Flowery and Woody-Like Odorant Ketones via Corey-Chaykovsky Oxiranylation: Irones and Analogues," Helvetica Chimica Acta, 76:2070-2088 (1993).
Fehr et al., "Highly Enantioselective Protonation of Thiol Ester Enolates," Angew. Chem. Int. Ed. Engl., 32(7):1042-1044 (1993).
Makin et al., "Cyclization of Analogs of Pseudoionone and Citral," J. Gen. Chem. USSR, 30:1491-1496 (1960).
Royals, "The Isomeric Citrylideneacetic Acids," J. Am. Chem. Soc., 69 (4):841-844 (1947).

*Primary Examiner* — John Hardee
(74) *Attorney, Agent, or Firm* — Winston & Strawn LLP

(57) ABSTRACT

The present invention relates to certain ester and nitrile derivatives of formula (I):

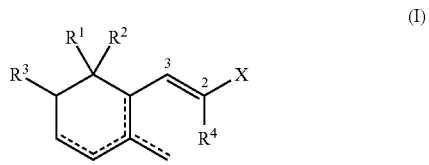

wherein one dotted line represents a carbon-carbon single or double bond and the other dotted lines each represent a carbon-carbon single bond;
$R^1$ is a hydrogen atom or a methyl group, $R^2$ is a methyl or ethyl group, $R^3$ is a hydrogen atom or a methyl group, $R^4$ is a hydrogen atom or a methyl group or said $R^4$ taken together with the bond between carbon atom 2 and 3 form a cyclopropane; and
X represents a CN or a COOR$^5$ group, $R^5$ representing a $C_{1-5}$ alkyl group; with the compound being in the form of any one of its pure stereoisomers or mixtures thereof. These compounds are useful perfuming ingredients.

19 Claims, No Drawings

CARBOXYLIC DERIVATIVES AS VIOLET AND/OR WOODY ODORANT

This application is a 371 filing of International Patent Application PCT/IB2010/051367, filed Mar. 30, 2010.

TECHNICAL FIELD

The present invention relates to the field of perfumery. More particularly, it concerns some ester and nitrile derivatives, as defined herein below, which are useful perfuming ingredients.

The present invention concerns the use of said compounds in the perfumery industry as well as the compositions or articles containing said compounds.

PRIOR ART

To the best of our knowledge, the compounds of the present invention are all new, except the various stereoisomers of ethyl 3-(2,2,6-trimethylcyclohexyl)-2-propenoate, e.g. reported in EP 456932 as chemical intermediates. This prior art document does not report or suggest any organoleptic properties of the compound of formula (I), or any use of said compound in the field of perfumery.

Amongst the known perfuming ingredients with a similar structure, one may cite the irones and the ionones (e.g. see Arctander's book cited herein below) family which are the closest ones and the most used. However, these compounds are ketones, and once again do not anticipate the present invention.

DESCRIPTION OF THE INVENTION

We have now surprisingly discovered that a compound of formula

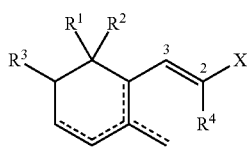

(I)

wherein one dotted line represents a carbon-carbon single or double bond and the other dotted lines a carbon-carbon single bond;
$R^1$ is a hydrogen atom or a methyl group, $R^2$ is a methyl or ethyl group, $R^3$ is a hydrogen atom or a methyl group;
$R^4$ is a hydrogen atom or a methyl group or said $R^4$ taken together with the bond between carbon atom 2 and 3 form a cyclopropane; and
X represents a CN or a $COOR^5$ group, $R^5$ representing a $C_{1-5}$ alkyl group;
can be used as perfuming ingredient, for instance to impart odor notes of the woody and/or violet type.

For the sake of clarity, by the expression "one dotted line represents a carbon-carbon single or double bond and the other dotted lines a carbon-carbon single bond", or the similar, it is meant the normal meaning understood by a person skilled in the art, i.e. that the whole bonding (solid and dotted lines) between the carbon atoms connected by said dotted lines, e.g. carbon 1' and 2', is a carbon-carbon single or double bond.

According to a particular embodiment of the invention, said compound (I) is of formula

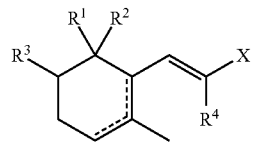

(II)

wherein one dotted line represents a carbon-carbon single or double bond and the other dotted lines a carbon-carbon single bond;
$R^1$ is a hydrogen atom or a methyl group, $R^2$ is a methyl or ethyl group, $R^3$ is a hydrogen atom or a methyl group;
$R^4$ is a hydrogen atom or a methyl group; and
X represents a CN or a $COOR^5$ group, $R^5$ representing a $C_{1-3}$ alkyl group.

According to any one of the above embodiments, $R^2$ and $R^2$ represent each a methyl group. According to any one of the above embodiments, all dotted lines represent a carbon-carbon single bond.

According to a particular embodiment of the invention, said compound (I) is of formula

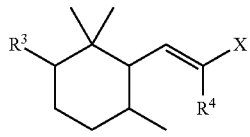

(III)

wherein $R^3$ is a hydrogen atom or a methyl group;
$R^4$ is a hydrogen atom or a methyl group; and
X represents a CN or a $COOR^5$ group, $R^5$ representing a $C_{1-3}$ alkyl group.

According to any one of the above embodiments, $R^4$ represents a hydrogen atom. According to any one of the above embodiments, $R^3$ represents a methyl atom. According to any one of the above embodiments, $R^5$ represents a methyl, ethyl or iso-propyl group, and in particular a methyl or ethyl group.

According to any one of the above embodiments, said invention's compound is a $C_{13}$, $C_{14}$ or $C_{15}$ compound.

According to any one of the above embodiments, said invention's compound can be in the form of any one of its stereoisomers, or enantiomers, or in the form of a mixture thereof. According to any one of the above embodiments, and in particular when all dotted lines represent a single bond, said compound is in the form of a mixture of stereoisomers comprising more than 50% (w/w) of the stereoisomer wherein the substituents at position 1 and 6 of the cyclohexane ring are in a trans relative configuration, and when $R^3$ is a methyl group preferably the substituents at position 3 and 6 of the cyclohexane ring are also in a trans relative configuration.

The compound of formula (I), (II) or (III), wherein $R^5$ represents a $C_{1-3}$ alkyl group is also an object of the invention, expect for ethyl 3-(2,2,6-trimethylcyclohexyl)-2-propenoate and its stereoisomers, which are described in the literature.

Amongst the invention's compounds, one may cite methyl (2E)-3-(2,2,c-3,t-6-tetramethyl-r-1-cyclohexyl)acrylate, which is one of the most appreciated by the perfumer. This compound possesses a powerful woody and ambery note and, at the same time, an elegant powdery/violet aspect. The odor of said compound is much more ambery/woody and violet than the equivalent irone which is more orris-balsamic.

Amongst the invention's compounds, one may cite also methyl (2E)-3-(2,2,t-3,c-6-tetramethyl-r-1-cyclohexyl)acrylate, which is also one of the most appreciated by the perfumer. This compound possesses an odor close to the one of its above-mentioned stereoisomer, but distinguishes itself by having a more pronounced woody and ambery note.

Furthermore, one may cite also methyl (2E)-3-[(1RS,3RS,6RS)-2,2,3,6-tetramethylcyclohexyl]acrylonitrile, which is also one of the most appreciated by the perfumer. This compound nitrile possesses a nice and pronounced woody/sandalwood note associated with ambergris and a violet/orris-like note, and some earthy bottom notes. The odor of said nitrile is more sandalwood/woody and as much violet as the equivalent irone which is more orris-balsamic Other compounds of formula (I) are also described in Table (I) herein below, together with their odors:

TABLE 1

Structure and odor characteristics of the invention's compounds

| Structure of compound (I) | Odor |
|---|---|
| methyl trans-(E)-3-(2,2,6-trimethyl-1-cyclohexyl)-2-propenoate | Woody, violet, and a fruity aspect |
| methyl (E)-3-(2,5,6,6-tetramethyl-1-cyclohexen-1-yl)-2-propenoate | Floral/violet note with a woody connotation |
| ethyl (E)-2-methyl-3-(2,6,6-trimethyl-2-cyclohexen-1-yl)-2-propenoate | Woody, ambery and violet/powdery notes with a soapy aspect |
| trans (2E)-3-(2,6,6-trimethylcyclohexyl)acrylonitrile | Violet, orris, woody, cellar notes |
| butyl (2E)-3-(2,6,6-trimethyl-2-cyclohexen-1-yl)-2-propenoate | Violet/powdery notes, with a woody aspect |

According to a particular embodiment of the invention, the compounds having the unusual combination of wood, ambery, violet notes are particularly useful for the functional perfumery, but can be used also in fine perfumery.

The invention's compounds are in general also characterized by an excellent tenacity and substantively on fabrics and hairs.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualitat, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a fine or functional perfumery base;
is also an object of the present invention.

For the sake of clarity, it has to be mentioned that, by "fine or functional perfumery base" we mean here a consumer product which is compatible with perfuming ingredients and is expected to deliver a pleasant odor to the surface to which it is applied (e.g. skin, hair, textile, or home surface). In other words, a consumer product for the purpose of perfuming according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the fine or functional perfumery base do not warrant a more detailed description here, which in any case would not be exhaustive, the skilled person being able to select them on the basis of his general knowledge and according to the nature and the desired effect of said product.

Non-limiting examples of suitable fine or functional perfumery base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.1% to 15% by weight, or even more, of the compounds of the invention based on the weight of the composition into which they are incorporated. Concentrations lower than these, such as in the order of 0.001% to 5% by weight, can be used when these compounds are incorporated into perfumed articles, percentage being relative to the weight of the article.

The invention's compounds can be prepared according to a method comprising a Wittig reaction between an adequate phosphonate and the adequate aldehyde of formula

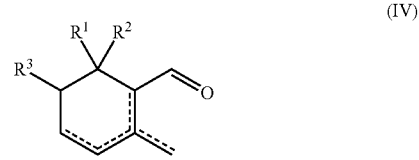

(IV)

wherein $R^1$, $R^2$, and $R^3$, as well as the dotted lines, have the meaning indicated in formula (I) herein above.

Specific examples are provided herein below in the Examples.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Synthesis of Compounds of Formula (I)

Preparation of (2E)-3-[(1RS,3RS,6RS)-2,2,3,6-tetramethylcyclohexyl]acrylonitrile A solution of EtONa (21 g, 21% in EtOH) was added to a solution of (3RS,6RS)-2,2,3,6-tetramethyl-2-cyclohexanecarbaldehyde [see C. Chapuis, R. Brauchli, *Helv. Chim. Acta* 1993, 76, 2070] (10 g, 59 mmol) and diethyl-cyanomethylphosphonate (11.5 g, 65 mmol) in pentane (80 ml). After 18 hours at 38° C. the reaction mixture was diluted with Et$_2$O, extracted to neutrality with H$_2$O, dried (Na$_2$SO$_4$), concentrated and bulb-to-bulb distilled to afford the pure desired product in 53% yield after column chromatography on SiO$_2$ (cyclohexane/Et$_2$O 9:1).

Bp: 50°/0.13 mbar
$^1$H-NMR: 6.54 (dd, J=10, 17, 1H); 5.27 (d, J=17, 1H); 1.74 (m, 1H); 1.57-1.40 (m, 2H); 1.32-1.15 (m, 3H); 1.05-0.9 (m, 1H); 0.84 (d, J=7, 3H); 0.83 (s, 3H); 0.75 (d, J=7, 3H); 0.74 (s, 3H).
$^{13}$C-NMR: 158.1 (d); 117.6 (s); 101.1 (d); 61.1 (d); 41.7 (d); 36.8 (s); 35.2 (t); 31.2 (d); 30.4 (t); 27.8 (q); 21.5 (q); 16.1 (q); 14.3 (q). MS: 191 (17, M$^{+\cdot}$), 176 (100), 148 (40), 123 (57), 121 (30), 109 (27), 97 (153), 94 (90), 83 (82), 69 (58), 55 (58), 41 (45).

Preparation of methyl (2E)-3-(2,2,c-3,t-6-tetramethyl-r-1-cyclohexyl)acrylate

MeONa (1.25 g, 23 mmol) was added to a solution of (3RS,6RS)-2,2,3,6-tetramethyl-2-cyclohexanecarbaldehyde (3.0 g, 18 mmol) and trimethylphosphonoacetate (4.5 g, 25 mmol) in pentane (40 ml). After 18 hours at reflux, the cold solution was diluted with Et$_2$O and extracted to neutrality with H$_2$O. The organic phase was dried (Na$_2$SO$_4$), concentrated and bulb-to-bulb distilled to afford the pure desired product in 57% yield.

Bp: 64°/0.13 mbar.
$^1$H-NMR: 6.79 (dd, J=8, 15, 1H); 5.77 (d, J=15, 1H); 3.73 (s, 3H); 1.72 (m, 1H); 1.58-1.39 (m, 3H); 1.33-1.17 (m, 2H); 1.05-0.9 (m, 1H); 0.84 (d, J=7, 3H); 0.82 (s, 3H); 0.75 (s, 3H); 0.73 (d, J=7, 3H).
$^{13}$C-NMR: 166.8 (s); 151.4 (d); 122.8 (d); 59.7 (d); 51.3 (q); 41.8 (d); 36.7 (s); 35.4 (t); 31.3 (d); 30.6 (t); 27.9 (q); 21.7 (q); 16.2 (q); 14.4 (q). MS: 224 (9, M$^+$), 193 (15), 181 (40), 153 (60), 127 (87), 111 (66), 100 (45), 95 (67), 81 (62), 69 (53), 67 (60), 55 (100), 41 (94).

Preparation of methyl (2E)-3-(2,2,t-3,c-6-tetramethyl-r-1-cyclohexyl)acrylate

MeONa (1.25 g, 23 mmol) was added to a solution of (3SR,6SR)-2,2,3,6-tetramethyl-2-cyclohexanecarbaldehyde [see C. Chapuis, R. Brauchli, *Helv. Chim. Acta* 1993, 76, 2070.] (3.0 g, 18 mmol) and trimethylphosphonoacetate (4.5 g, 25 mmol) in pentane (40 ml). After 18 h at reflux the cold solution was diluted with Et$_2$O and extracted to neutrality with H$_2$O. The organic phase was dried (Na$_2$SO$_4$), concentrated and bulb-to-bulb distilled to afford the pure desired product in 27% yield.

Bp: 65°/0.08 mbar.
$^1$H-NMR: 6.80 (dd, J=8, 15); 5.77 (d, J=15, 1H); 3.74 (s, 3H); 1.89 (m, 1H); 1.59-1.39 (m, 3H); 1.33-1.17 (m, 2H); 1.05-0.9 (m, 1H); 0.90 (s, 3H); 0.84 (d, J=7, 3H); 0.78 (s, 3H); 0.73 (d, J=7, 3H).
$^{13}$C-NMR: 166.7 (s); 148.9 (d); 123.2 (d); 57.4 (d); 51.3 (q); 36.5 (s); 35.4 (d); 31.2 (t); 30.6 (d); 30.1 (t); 28.9 (q); 21.2 (q); 20.9 (q); 15.9 (q). MS: 224 (6, M$^{+\cdot}$), 193 (12), 181 (40), 153 (60), 127 (89), 111 (62), 95 (66), 81 (62), 67 (58), 55 (100), 41 (90).

Preparation of methyl (2E)-3-(2,5,6,6-tetramethyl-1-cyclohexen-1-yl)-2-propenoate Obtained in 11% yield from 2,5,6,6-tetramethyl-1-cyclohexene-1-carbaldehyde [see C. Chapuis, R. Brauchli, *Helv. Chim. Acta* 1993, 76, 2070.] similarly to the procedure used for methyl (2E)-3-(2,2,c-3,t-6-tetramethyl-r-1-cyclohexyl)acrylate.

Bp: 60°/0.12 mbar,
$^1$H-NMR: 7.41 (d, J=16.1, 1H); 5.79 (d, J=16.1, 1H); 3.76 (s, 3H); 2.05 (m, 2H); 1.73 (brs, 3H); 1.61-1.37 (m, 3H); 1.05 (s, 3H); 0.90 (d, J=6.5, 3H); 0.90 (s, 3H).
$^{13}$C-NMR: 167.6 (s); 145.5 (d); 136.2 (s); 133.6 (s); 122.3 (d); 51.4 (q); 39.0 (d); 37.2 (s); 32.2 (t); 27.5 (q); 26.7 (t); 22.0 (q); 21.8 (q); 16.2 (q).

Preparation of methyl trans-(2E)-3-(2,2,6-trimethyl-1-cyclohexyl)-2-propenoate

Trimethyl phosphonoacetate (200 g, 1.1 mol) was added dropwise to a suspension of NaH (44 g, 55% in oil, 1.1 mol) in iPr$_2$O (1600 ml). After 2.5 hours, a solution of trans 2,3,6-trimethyl-2-cyclohexanecarbaldehyde [see C. Chapuis, R. Brauchli, *Helv. Chim. Acta* 1993, 76, 2070.] (91 g, 0.59 mol) in iPr$_2$O (400 ml) was added dropwise. After 18 hours at 20° C., the reaction mixture was poured onto ice and extracted to neutrality with brine, dried (Na$_2$SO$_4$), concentrated and distilled through a 15 cm Vigreux column to afford the pure desired product in 41% yield.

Bp 104° C./5.2 mbar.
$^1$H-NMR: (60 MHz) 0.65-2.2 (m, 17H); 3.72 (s, 3H); 5.79 (d, J=16, 1H); 6.79 (dd, J=10, 16, 1H).
$^{13}$C-NMR: 166.8 (s); 151.3 (d); 122.5 (d); 58.3 (d); 51.4 (q); 41.3 (t); 35.2 (t); 33.8 (s); 31.4 (q); 31.3 (d); 21.8 (t); 21.5 (q); 20.5 (q).

Preparation of ethyl (2E)-2-methyl-3-(2,6,6-trimethyl-2-cyclohexen-1-yl)-2-propenoate EtONa (1.56 g, 23 mmol) was added to a solution of 2,3,6-trimethyl-2-cyclohex-1-enecarbaldehyde [see C. Fehr, I. Stempf, J. Galindo, *Angew. Chem.* 1993, 105, 1091] (2.74 g, 18 mmol) and triethylphosphonopropionate (4.85 g, 25 mmol) in pentane (40 ml). After 18 h at 20° C., the cold solution was diluted with Et$_2$O and extracted to neutraltity with H$_2$O. The organic phase was dried (Na$_2$SO$_4$), concentrated and purified by column chromatography on SiO$_2$ (cyclohexane/AcOEt 97:3) to afford the pure desired product in 23% yield.

Bp: 90° C./0.08 mbar.
$^1$H-NMR: 6.57 (d, J=12, 1H); 5.43 (s, 1H); 4.19 (q, J=7, 2H); 2.57 (d, J=12, 1H); 2.05 (brs, 2H); 1.93 (s, 3H); 1.55 (s, 3H); 1.30 (t, J=7, 3H); 0.92 (s, 3H); 0.82 (s, 3H).

$^{13}$C NMR: 168.3 (s); 143.5 (d); 133.4 (s); 128.0 (s); 121.8 (d); 60.4 (t); 49.9 (d); 32.7 (s); 31.8 (t); 27.2 (q); 26.9 (q); 23.1 (t); 22.8 (q); 14.3 (q); 12.9 (q).

Preparation of trans (2E)-3-(2,6,6-trimethylcyclohexyl)acrylonitrile $^t$BuOK (5.6 g, 50 mmol) was added portion wise to a solution of trans dihydrocyclocitral (7.7 g, 50 mmol) and diethylcyanomethylphosphonate (12.4 g, 70 mmol) in toluene (100 ml). After stirring 3 days at 20° C., the reaction mixture was washed to neutrality with H$_2$O, dried (MgSO$_4$), concentrated and bulb-to bulb distilled to afford the desired nitrile in 76.4% yield.

Bp: 80° C./0.13 mbar.

$^1$H-NMR: 6.48 (dd, J=10.2, 16.1, 1H); 5.27 (d, J=16.1, 1H); 1.78-1.71 (m, 2H); 1.54-1.40 (m, 4H); 1.21-1.09 (m, 2H); 0.87 (s, 3H); 0.84 (s, 3H); 0.77 (d, J=6.5, 3H).

$^{13}$C-NMR: 117.5 (s); 158.0 (d); 100.9 (d); 59.8 (d); 41.0 (t); 35.0 (t); 33.9 (s); 31.2 (d); 31.2 (q); 21.6 (t); 21.4 (q); 20.4 (q).

Preparation of butyl (2E)-3-(2,6,6-trimethyl-2-cyclohexen-1-yl)-2-propenoate

α-Cyclocitrylidene acetic acid (E. E. Royals, *J. Am. Chem. Soc.* 1947, 69, 841) (100 g, 515 mmol) was dissolved in a mixture of n-butanol (67 g, 905 mmol) and toluene (100 ml). After addition of pTsOH (1.25 g, 6.6 mmol), the mixture was heated to reflux and H$_2$O was removed by co-distillation with a Dean-Stark apparatus. When no more H$_2$O separated (6 h), toluene (90 ml) were distilled out and the remaining solution was poured into H$_2$O. Extraction with pentane afforded after usual work-up and distillation the pure n-butyl ester (100 g, 400 mmol, 77.7%).

Bp: 85-89° C./0.07 mbar.

$^1$H-NMR: 6.79 (dd, J=10.5, 15.5, 1H); 5.79 (d, J=15.5, 1H); 5.48 (brs, 1H); 4.14 (t, J=7, 2H); 2.27 (brd, J=9.5, 1H); 2.03 (brs, 2H); 1.69-1.61 (m, 3H); 1.57 (d, J=1.5, 3H); 1.45-1.37 (q, J=7, 2H); 1.23-1.16 (m, 1H); 0.97 (t, J=7, 3H); 0.92 (s, 3H); 0.85 (s, 3H).

$^{13}$C-NMR: 166.5 (s); 149.7 (d); 132.1 (s); 122.5 (d); 122.3 (d); 64.2 (t); 54.0 (d); 32.5 (s); 31.2 (t); 30.8 (t); 27.8 (q); 26.9 (q); 23.0 (t); 22.8 (q); 19.2 (t); 13.8 (q).

Preparation of ethyl (2E)-3-(6-ethyl-2,6-dimethyl-2-cyclohexen-1-yl)-2-methyl-2-propenoate Obtained in 21% yield from (6-ethyl-2,6-dimethyl-2-cyclohexen-1-yl)-carbaldehyde (see Makin et al. *J. Gen. Chem. USSR* 1960, 30, 1491) as a 1:1 mixture of stereoisomers according to the procedure used for ethyl (E)-2-methyl-3-(2, 6,6-trimethyl-2-cyclohexen-1-yl)-2-propenoate with triethylphosphonopropionate.

Bp: 95° C./0.08 mbar.

$^1$H-NMR: 6.58 (t, J=12, 1H); 5.43 (s, 1H); 4.19 (q, J=7, 2H); 2.6 (dd, J=15, 27, 1H); 2.08-1.97 (m, 3H); 1.94 (s, 3H); other diastereoisomer 1.91 (s, 3H); 1.54 (s, 3H); 1.48-1.35 (m, 2H); 1.3 (t, J=7, 3H); 1.17 (q, J=7, 2H); 0.87 (s, 3H); 0.83 (t, J=7, 3H); 0.76 (s, 3H).

$^{13}$C NMR: 168.3 (s); 143.5 (d); 133.2 (s); 128.0 (s); 122.0 (d); 60.4 (t); 48.5 (d); 35.3 (s); 31.0 (t); 28.8 (t); 23.2 (q); 22.8 (q); 22.8 (t); 14.3 (q); 12.9 (q); 7.9 (q).

Example 2

Preparation of a Perfuming Composition

A perfuming composition for a fabric softener was prepared by admixing the following ingredients:

| Ingredient | Parts by weight |
|---|---|
| Benzyl acetate | 500 |
| Linalyl acetate | 100 |
| Cis-3-hexenol acetate | 10 |
| Styrallyl acetate | 20 |
| Verdyl acetate | 600 |
| Anisic aldehyde | 600 |
| Aldehyde C 10 | 10 |
| Hexylcinnamic aldehyde | 100 |
| Methyl anthranilate | 300 |
| Lemon essential oil | 100 |
| Citronellol | 70 |
| 10%* Damascone Alpha | 40 |
| Dihydromyrcenol | 100 |
| Geraniol | 60 |
| Hedione ®[1] | 400 |
| Ionone alpha | 150 |
| Iso E ® Super[2] | 200 |
| Isoeugenol | 40 |
| Acetyl diisoamylene[3] | 450 |
| Lilial ®[4] | 300 |
| Linalool | 300 |
| Methylnaphtylketone | 50 |
| Muscenone Delta[5] | 50 |
| Phenethylol | 120 |
| Phenylethyl phenylacetate | 150 |
| 3-Methyl-5-phenylpentanol | 100 |
| Orange essential oil | 50 |
| Verdyl propionate | 200 |
| Benzyl salicylate | 120 |
| Terpineol Alpha | 60 |
| 10% * 2,4-Dimethyl-3-cyclohexene-1-carbaldehyde | 50 |
| | 5400 |

*in dipropyleneglycol
[1] methyl dihydrojasmonate; origin: Firmenich SA, Geneva, Switzerland
[2] 1-(octahydro-2,3,8,8-tetramethyl-2-naphtalenyl)-1-ethanone; origin: International Flavor & Fragrance, USA
[3] origin: International Flavor & Fragrance, USA
[4] 3-(4-tert-butylphenyl)-2-methylpropanal; origin: Givaudan, Vernier, Switzerland
[5] 3-methyl-(4)-cyclopentadecenone; origin: Firmenich SA, Geneva, Switzerland The addition of 600 parts by weight of methyl (2E)-3-(2, 2,c-3,t-6-tetramethyl-r-1-cyclohexyl)acrylate to the above-described composition conferred a very nice woody, powdery connotation.

The addition of 600 parts by weight of methyl (2E)-3-(2, 2,t-3,c-6-tetramethyl-r-1-cyclohexyl)acrylate the composition acquired a character more woody, ambery et slightly less violet/powdery than the one where the (2E)-3-(2,2,c-3,t-6-tetramethyl-r-1-cyclohexyl)acrylate were added.

When instead of the invention's compound was used the same amount of ionone or methyl ionone, the effect was much less woody and much more powdery. When instead of the invention's compound was used the same amount of irone, the effect was much less woody and much more orris and balsamic.

Example 3

Preparation of a Perfuming Composition

An "eau de toilette" for woman was prepared by admixing the following ingredients:

| Ingredient | Parts by weight |
| --- | --- |
| Cinnamic Alcohol | 20 |
| Amione ®[1)] | 10 |
| Citronellol | 80 |
| Coumarine | 150 |
| 2-Methyl-4-(2,2,3-trimethyl-3-cyclo penten-1-yl)-4-penten-1-ol | 100 |
| 70%* Galaxolide ®[2)] | 250 |
| Geraniol | 100 |
| Geranium essential oil | 30 |
| 1,3-Benzodioxole-5-carbaldehyde[3)] | 60 |
| Hydroxycitronellal | 110 |
| Iso E ® Super[4)] | 240 |
| Lilyflore ®[5)] | 50 |
| Linalool | 100 |
| Muscenone Delta[6)] | 100 |
| Phenethylol | 120 |
| Vanilline | 30 |
| Vertofix ® Coeur[7)] | 300 |
| | 1850 |

*in myristate d'isopropyle
[1)]allyl ionone; origin: Givaudan, Vernier, Switzerland
[2)]1,3,4,6,7,8-hexahydro-4,6,6,7,8,8-hexamethyl-cyclopenta-g-2-benzopyrane; origin: International Flavors & Fragrances, USA
[3)]origin: Firmenich SA, Geneva, Switzerland
[4)]1-(octahydro-2,3,8,8-tetramethyl-2-naphtalenyl)-1-ethanone; origin: International Flavors & Fragrances, USA
[5)]2,5-dimethyl-2-indanmethanol; origin: Firmenich SA, Geneva, Switzerland
[6)]3-methyl-(4)-cyclopentadecenone; origin: Firmenich SA, Geneva, Switzerland
[7)]methyl cedryl ketone; origin: International Flavor & Fragrance, USA The addition of 150 parts by weight of methyl (2E)-3-(2,2,c-3,t-6-tetramethyl-r-1-cyclohexyl)acrylate to the above-described eau de toilette conferred a wonderful powdery, woody touch, while when it was used methyl (2E)-3-(2,2,t-3,c-6-tetramethyl-r-1-cyclohexyl)acrylate the cologne acquired a woody touch and then became more powdery.

Once again these effects were not obtainable using the ionones, methylionones, or the irones.

What is claimed is:

1. A compound of formula

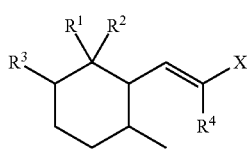

(I)

wherein:
$R^1$ is a hydrogen atom or a methyl group, $R^2$ is a methyl or ethyl group, $R^3$ is a hydrogen atom or a methyl group;
$R^4$ is a hydrogen atom or a methyl group or $R^4$ taken together with the bond between carbon atoms 2 and 3 forms a cyclopropane; and
X represents a CN or a $COOR^5$ group, $R^5$ representing a $C_{1-3}$ alkyl group;
in the form of any one of its pure stereoisomers or mixtures thereof;
provided that ethyl 3-(2,2,6-trimethylcyclohexyl)-2-propenoate and its stereoisomers are excluded.

2. A compound according to claim 1, having the formula:

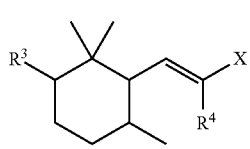

(III)

wherein $R^3$ is a hydrogen atom or a methyl group;
$R^4$ is a hydrogen atom or a methyl group; and
X represents a CN or a $COOR^5$ group, $R^5$ representing a $C_{1-3}$ alkyl group.

3. A perfuming composition comprising
i) at least compound of formula (I) as defined in claim 2;
ii) at least one ingredient selected from the group consisting of a perfumery carrier and a perfumery base; and
iii) optionally at least one perfumery adjuvant.

4. A perfumed article comprising:
i) at least one compound of formula (I) as defined in claim 2; and
ii) a fine or functional perfumery base.

5. A perfumed article according to claim 4, wherein the fine or functional perfumery base is a perfume, a fabric care product, a body-care product, an air care product or a home care product.

6. A perfumed article according to claim 4, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

7. A compound according to claim 1, specifically as is methyl (2E)-3-(2,2,c-3,t-6-tetramethyl-r-1-cyclohexyl)acrylate, methyl (2E) -3-(2,2,t-3,c-6-tetramethyl-r-1-cyclohexyl) acrylate or methyl (2E)-3-[(1RS,3RS,6RS)-2,2,3,6-tetramethylcyclohexyl]acrylonitrile.

8. A perfuming composition comprising
i) at least one compound according to claim 1;
ii) at least one ingredient selected from the group consisting of a perfumery carrier and a perfumery base; and
iii) optionally at least one perfumery adjuvant.

9. A perfumed article comprising:
i) at least one compound according to claim 1; and
ii) a fine or functional perfumery base.

10. A perfumed article according to claim 9, wherein the fine or functional perfumery base is a perfume, a fabric care product, a body-care product, an air care product or a home care product.

11. A perfumed article according to claim 9, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

12. A method to confer, enhance, improve or modify the odor properties of a perfuming composition or of a perfumed article, which method comprises adding to the composition or article an effective amount of at least one compound of formula (I):

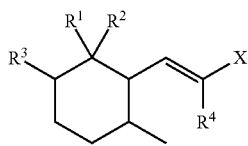

(I)

wherein;

$R^1$ is a hydrogen atom or a methyl group, $R^2$ is a methyl or ethyl group, $R^3$ is a hydrogen atom or a methyl group;

$R^4$ is a hydrogen atom or a methyl group or $R^4$ taken together with the bond between carbon atoms 2 and 3 forms a cyclopropane; and X represents a CN or a COOR$^5$ group, $R^5$ representing a $C_{1-5}$ alkyl group;

with the compound being in the form of any one of its pure stereoisomers or mixtures thereof.

13. A method according to claim 12, wherein the compound has formula (II):

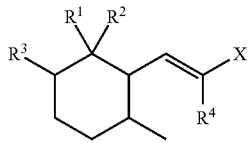

(II)

wherein;

$R^1$ is a hydrogen atom or a methyl group, $R^2$ is a methyl or ethyl group, $R^3$ is a hydrogen atom or a methyl group;

$R^4$ is a hydrogen atom or a methyl group; and

X represents a CN or a COOR$^5$ group, $R^5$ representing a $C_{1-3}$ alkyl group.

14. A method according to claim 12, wherein the compound has formula (III):

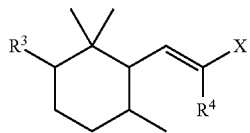

(III)

wherein $R^3$ is a hydrogen atom or a methyl group;

$R^4$ is a hydrogen atom or a methyl group; and

X represents a CN or a COOR$^5$ group, $R^5$ representing a $C_{1-3}$ alkyl group.

15. A method according to claim 12, wherein the compound is methyl (2E)-3-(2,2,c-3,t-6-tetramethyl-r-1-cyclohexyl)acrylate, methyl (2E) -3-(2,2,t-3,c-6-tetramethyl-r-1-cyclohexyl)acrylate or methyl (2E)-3-[(1RS,3RS,6RS)-2,2,3,6-tetramethylcyclohexyl]acrylonitrile.

16. A method according to claim 12, wherein the compound is added to the composition or article in a perfuming composition comprising
 i) the compound;
 ii) at least one ingredient selected from the group consisting of a perfumery carrier and a perfumery base; and
 iii) optionally at least one perfumery adjuvant.

17. A method according to claim 12, wherein the compound is added to an article comprising a fine or functional perfumery base.

18. A method according to claim 17, wherein the fine or functional perfumery base is a perfume, a fabric care product, a body-care product, an air care product or a home care product.

19. A method according to claim 17, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

* * * * *

UNITED STATES PATENT AND TRADEMARK OFFICE
CERTIFICATE OF CORRECTION

| | | |
|---|---|---|
| PATENT NO. | : 8,183,194 B2 | Page 1 of 1 |
| APPLICATION NO. | : 13/255298 | |
| DATED | : May 22, 2012 | |
| INVENTOR(S) | : Chapuis et al. | |

It is certified that error appears in the above-identified patent and that said Letters Patent is hereby corrected as shown below:

On the Title Page:
Item (56) References Cited, OTHER PUBLICATIONS, "International Search Report" reference, change "PCTAB2010/051367" to -- PCT/IB2010/051367 --.

Column 13:
Line 16 (claim 12, first line after formula (I)), change "wherein;" to -- wherein: --.
Line 38 (claim 13, first line after formula (II)), change "wherein;" to -- wherein: --.

Signed and Sealed this
Tenth Day of July, 2012

David J. Kappos
*Director of the United States Patent and Trademark Office*